(12) United States Patent
Goehring et al.

(10) Patent No.: US 7,259,176 B2
(45) Date of Patent: Aug. 21, 2007

(54) PROCESS FOR THE PREPARATION OF THE INSULIN SENSITIZER

(75) Inventors: Wolfgang Goehring, Steinen (DE); Ursula Hoffmann, Muttenz (CH); Michelangelo Scalone, Birsfelden (CH); Helmut Stahr, Loerrach (DE); Shaoning Wang, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 494 days.

(21) Appl. No.: 10/872,871

(22) Filed: Jun. 21, 2004

(65) Prior Publication Data

US 2004/0267023 A1     Dec. 30, 2004

(30) Foreign Application Priority Data

Jun. 26, 2003    (EP)   ............................. 03013491

(51) Int. Cl.
| | |
|---|---|
| A61K 31/381 | (2006.01) |
| A61K 31/422 | (2006.01) |
| C07D 263/30 | (2006.01) |
| C07D 277/04 | (2006.01) |

(52) U.S. Cl. ...................... 514/369; 514/374; 548/183; 548/235

(58) Field of Classification Search ................ 514/374, 514/369; 548/183, 235
See application file for complete search history.

(56) References Cited

U.S. PATENT DOCUMENTS 5,599,826 A    2/1997   Mertens et al.
6,441,185 B2 *   8/2002   Kuhnle et al. .............. 548/183

FOREIGN PATENT DOCUMENTS

WO    WO94/27995    12/1994
WO    WO 01/79202 A1    10/2001

OTHER PUBLICATIONS

Malamas, M.S. et al, Journal of Medicinal Chemistry, vol. 43, No. 5, (XP-002175477), pp. 995-1010 (2000).
Malamas, M.S. et al, Journal of Medicinal Chemistry, vol. 39, No. 1, (XP002093481), pp. 237-245 (1996).

* cited by examiner

*Primary Examiner*—Rebecca Anderson
*Assistant Examiner*—Shawquia Young
(74) *Attorney, Agent, or Firm*—George W. Johnston; Patricia S. Rocha-Tramaloni

(57) ABSTRACT

A novel process for the preparation of compounds of formula I

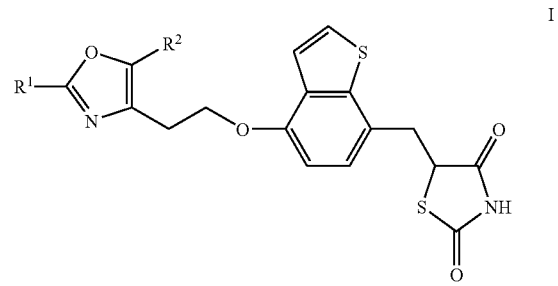

and optionally converting a compound of formula I into a pharmaceutically acceptable salt is disclosed. The compounds of formula I and the corresponding salts, e.g. the sodium salts, are pharmaceutically active substances. Processes for the creation of intermediates are also disclosed.

19 Claims, No Drawings

PROCESS FOR THE PREPARATION OF THE INSULIN SENSITIZER

BACKGROUND OF THE INVENTION

The present invention is concerned with a novel process for the preparation of thiazolidinedione derivatives, especially with the preparation of 5-{4-[2-(5-Methyl-2-phenyl-oxazol-4-yl)-ethoxy]-benzo[b]thiophen-7-ylmethyl}2,4-thiazolidinedione and its salts. 5-{4-[2-(5-Methyl-2-phenyl-oxazol-4-yl)-ethoxy]-benzo[b]thiophen-7-ylmethyl}2,4-thiazolidinedione and its salts, particularly the sodium salt, are pharmaceutically active compounds. These compounds are known in the art and are described for example in International Patent Application WO 94/27995. They are especially useful for the prophylaxis and/or treatment of diabetes mellitus type I and II.

Methods for the preparation of 5-{4-[2-(5-Methyl-2-phenyl-oxazol-4-yl)-ethoxy]-benzo[b]thiophen-7-ylmethyl}2, 4-thiazolidinedione have e.g. been described in WO 94/27995, WO 01/79202 and EP 1078923. However, these methods include a large number of individual reaction steps. Further, the methods known in the art exhibit a low yield or other disadvantages, which makes them unsuitable for the commercial large scale production of 5-{4-[2-(5-Methyl-2-phenyl-oxazol-4-yl)-ethoxy]-benzo[b]thiophen-7-ylmethyl}2,4-thiazolidinedione. A need exists for new methods of producing 5-{4-[2-(5-Methyl-2-phenyl-oxazol-4-yl)-ethoxy]-benzo[b]thiophen-7-ylmethyl}2,4-thiazolidinedione

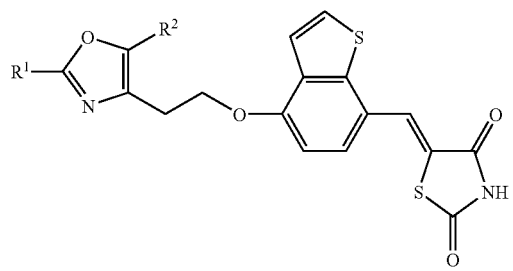

(I)

that are economical and result in high yield of product.

SUMMARY OF THE INVENTION

It has surprisingly been found that using the processes according to the present invention, 5-{4-[2-(5-Methyl-2-phenyl-oxazol-4-yl)-ethoxy]-benzo[b]thiophen-7-ylmethyl}2,4-thiazolidinedione can be prepared more economically with less process steps under moderate reaction conditions with an outstanding yield. Further, crude intermediate products can mostly be used in subsequent reaction steps without the need of any additional purification steps.

The present invention refers to a process for the preparation of compounds of formula (I)

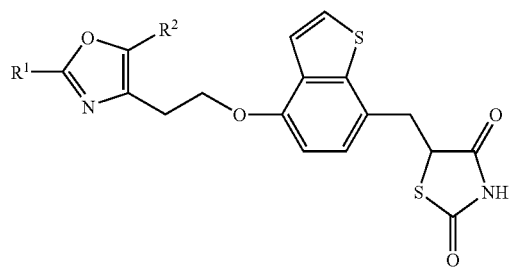

(I)

comprising reacting a compound of formula (II)

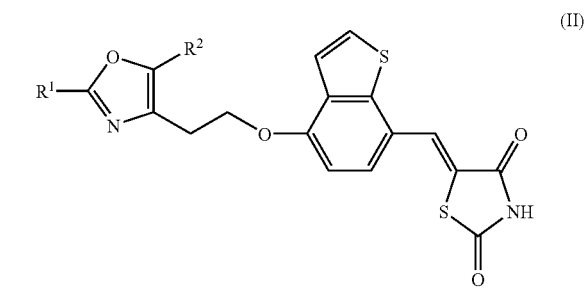

(II)

with a compound of formula (III)

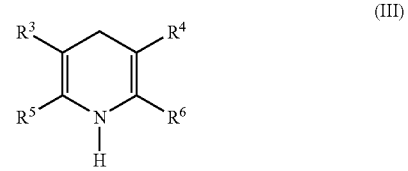

(III)

to yield the compound of formula (I), and optionally converting the compound of formula (I) into a pharmaceutically acceptable salt, wherein $R^1$ is aryl or heteroaryl, $R^2$ is lower-alkyl, $R^3$ is $COOR^7$, $R^4$ is $COOR^8$, $R^5$ and $R^6$ independently from each other are lower-alkyl, fluoro-lower-alkyl, aryl or —$CH_2$-aryl, $R^7$ and $R^8$ independently from each other are lower-alkyl, cycloalkyl, aryl or —$CH_2$-aryl, or $R^3$ and $R^5$ together are —CH=CH—CH=CH— to form a benzene ring together with the carbon atoms to which they are attached and $R^4$ and $R^6$ together are —CH=CH—CH=CH— to form a benzene ring together with the carbon atoms to which they are attached.

This process provides an efficient method for producing compounds of formula I. Compared to the processes known in the art, the process of the present invention exhibits a higher yield, moderate reaction conditions and other commercially relevant advantages. Another aspect of the present invention relates to a process for the preparation of compounds of formula IV

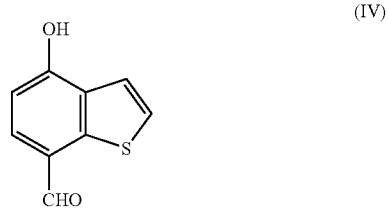

(IV)

comprising reacting a compound of formula V

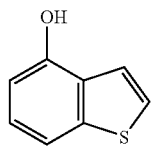

(V)

with glyoxylic acid to yield a compound of formula (VI)

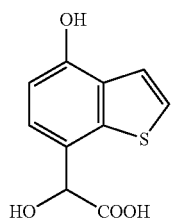

(VI)

and subsequent oxidative decarboxylation of the compound of formula (VI), to obtain the compound of formula (IV).

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "alkyl" refers to a branched or straight chain monovalent saturated aliphatic hydrocarbon radical of one to twenty carbon atoms, preferably one to sixteen carbon atoms.

The term "lower-alkyl" refers to a branched or straight chain monovalent alkyl radical of one to seven carbon atoms, preferably one to four carbon atoms. This term is further exemplified by such radicals as methyl, ethyl, n-propyl, isopropyl, i-butyl, n-butyl, t-butyl and the like with methyl and ethyl being preferred.

The term "fluoro-lower-alkyl" refers to lower-alkyl groups which are mono- or multiply substituted with fluorine. Examples of fluoro-lower-alkyl groups are e.g. $CF_3$, $CF_3CH_2$ and $(CF_3)_2CH$.

The term "alkoxy" refers to the group alkyl-O—, the term "lower alkoxy" to the group lower-alkyl-O—.

The term "cycloalkyl" refers to a monovalent carbocyclic radical of 3 to 10 carbon atom(s), preferably 3 to 6 carbon atoms, such as e.g. cyclopropyl, cyclobutyl, cyclopentyl or cyclohexyl.

The term "halogen" refers to fluorine, chlorine, and bromine, preferably to chlorine and bromine and more preferably to bromine.

The terms "primary amine", "secondary amine" and "tertiary amine" refer to the groups $NH_2R$, $NHR_2$ and $NR_3$ respectively, wherein the groups R, independently from each other can e.g. be lower-alkyl or aryl, preferably lower-alkyl. A preferred tertiary amine is tributylamine.

The term "aryl" relates to the phenyl or naphthyl group, preferably the phenyl group, which can optionally be mono- or multiply-substituted by substituents such as e.g. lower-alkyl, halogen, hydroxy, lower-alkoxy, CN and $CF_3$.

The term "heteroaryl" refers to an aromatic 5- or 6-membered ring which can contain 1 or 2 atoms selected from nitrogen, oxygen or sulphur such as furyl, pyridyl, 1,2-, 1,3- and 1,4-diazinyl, thiophenyl, isoxazolyl, oxazolyl or imidazolyl. A heteroaryl group may have a substitution pattern as described earlier in connection with the term "aryl".

The term "pharmaceutically acceptable salts" refers to salts of compounds of formula (I) with bases. Examples of such salts are alkaline, earth-alkaline and ammonium salts such as e.g. Na—, K—, Ca— and Trimethylammoniumsalt. Alkaline salts, particularly the Na-salt, are preferred.

In detail, the present invention refers to a process for the preparation of compounds of formula (I)

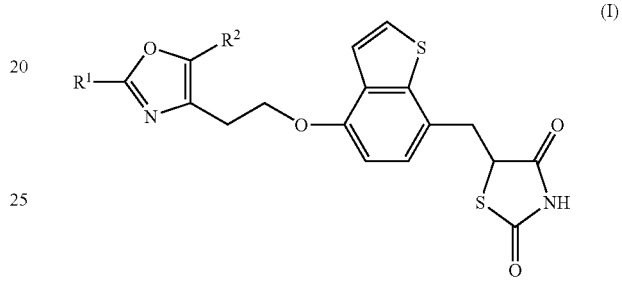

(I)

comprising reacting a compound of formula (II)

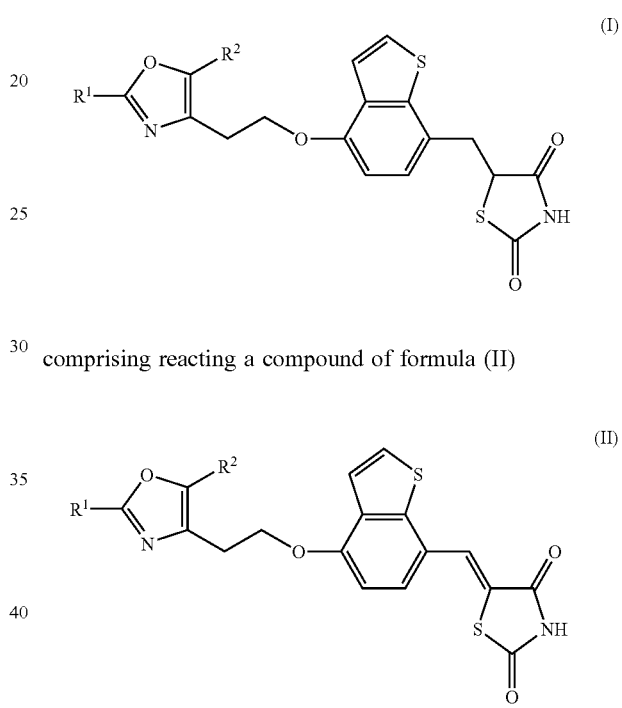

(II)

with a compound of formula (III)

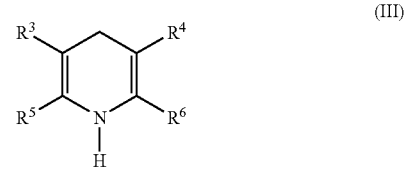

(III)

to yield the compound of formula (I), and optionally converting the compound of formula (I) into a pharmaceutically acceptable salt, wherein $R^1$ is aryl or heteroaryl, $R^2$ is lower-alkyl, $R^3$ is $COOR^7$, $R^4$ is $COOR^8$, $R^5$ and $R^6$ independently from each other are lower-alkyl, fluoro-lower-alkyl, aryl or —$CH_2$-aryl, $R^7$ and $R^8$ independently from each other are lower-alkyl, cycloalkyl, aryl or —CH$_2$-aryl, or $R^3$ and $R^5$ together are —CH=CH—CH=CH— to form a benzene ring together with the carbon atoms to which they are attached and $R^4$ and $R^6$ together are —CH=CH—CH=CH— to form a benzene ring together with the carbon atoms to which they are attached.

In a preferred embodiment of the present invention as described above $R^1$ is phenyl or thien-2-yl, more preferably phenyl.

Another preferred embodiment relates to a process as defined above, wherein $R^2$ is methyl.

In an especially preferred embodiment $R^1$ is phenyl and $R^2$ is methyl.

Preferably, $R^3$ is COOR$^7$, $R^4$ is COOR$^8$ and $R^7$ and $R^8$ are as defined above. Furthermore, a process as defined above, wherein $R^3$ is COOR$^7$, $R^4$ is COOR$^8$ and $R^7$ and $R^8$ independently from each other are lower-alkyl, particularly methyl, is preferred.

Preferably, $R^5$ and $R^6$ independently from each other are lower-alkyl, particularly methyl. In another preferred embodiment a process as defined above is carried out at a reaction temperature between 100° C. and 280° C., more preferably at a reaction temperature between 160° C. and 260° C. A process as defined above, which is carried out continuously at a reaction temperature between 220° C. and 250° C., constitutes an especially preferred embodiment of the present invention.

Preferably, a process as defined above is carried out in 1,3,5-trimethylbenzene, diphenylether or Dowtherm A as a solvent, particularly in 1,3,5-trimethylbenzene or diphenylether, more particularly in 1,3,5-trimethylbenzene or more particularly in diphenylether. A process as defined above, which is carried out in the presence of a base, is also preferred, particularly wherein the base is Hünig base, triethylamine or tributylamine.

A process as defined above, wherein the compound of formula (I) is converted into the sodium salt, is also preferred, more preferably wherein the compound of formula (I) is converted into the sodium salt by reaction with sodium hydroxide in THF.

Another aspect of the present invention relates to a process for the preparation of compounds of formula IV

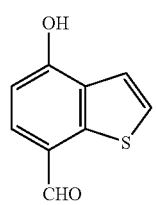

(IV)

comprising reacting a compound of formula V

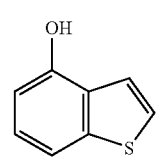

(V)

with glyoxylic acid to yield a compound of formula (VI)

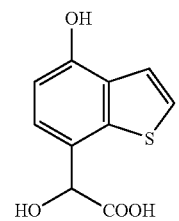

(VI)

and subsequent oxidative decarboxylation of the compound of formula (VI), to obtain the compound of formula (IV).

Preferably, in a process as defined above, the reaction of a compound of formula (V) with glyoxylic acid is carried out in an aqueous solution in the presence of a base. Preferred bases are NaOH, KOH, CsOH, Ca(OH)$_2$, tetrapropyl-NOH, trimethyl-benzyl-NOH, KO(tert.-butyl), DBU, tributylamine, more preferably KOH. Furthermore, a process as defined above, wherein the compound of formula (VI) is converted to a salt with a primary, secondary or tertiary amine and isolated, before the subsequent oxidative decarboxylation, is also preferred, particularly wherein the amine is a tertiary amine, especially tributylamine.

A process as defined above, wherein the oxidative decarboxylation is carried out with Fe$_2$(SO$_4$)$_3$ in a mixture of water and a cosolvent selected from the group consisting of CH$_3$CN, DMF, ethanol, isopropanol, acetone and isopropylacetate, is also preferred. If the compound of formula (VI) was converted to a salt as described above, the oxidative decarboxylation is preferably carried out in the presence of an acid. Preferred acids are HCl or H$_2$SO$_4$.

Another preferred embodiment of the present invention relates to a process as defined above for the preparation of compounds of formula (I)

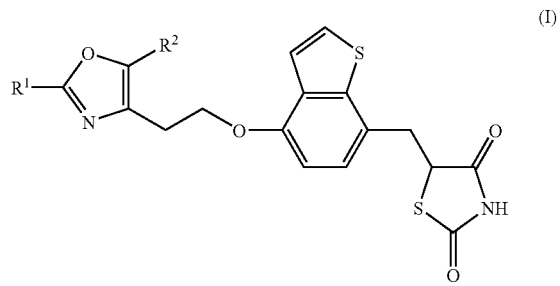

(I)

comprising preparation of a compound of formula (IV)

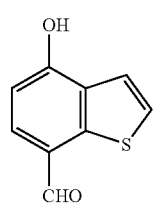

(IV)

by a process as defined above, reacting the compound of formula (IV) with a compound of formula (VII)

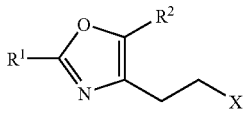
(VII)

wherein X is halogen or —O—SO$_2$—R$^9$, wherein R$^9$ is lower-alkyl, aryl or trifluoromethyl, to yield a compound of formula (VIII),

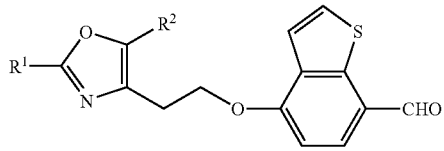
(VIII)

reacting the compound of formula (VIII) with thiazolidinedione to yield a compound of formula (II)

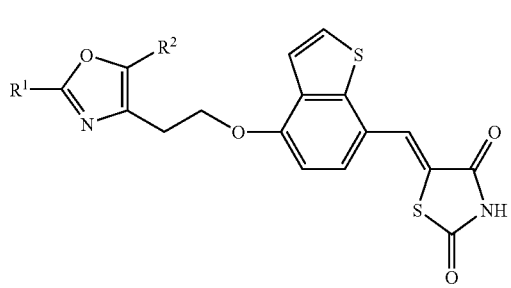
(II)

converting the compound of formula (II) to the compound of formula (I) by reacting the compound of formula II with the compound of formula III,

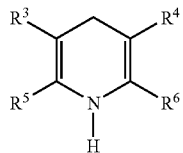
(III)

and optionally converting the compound of formula (I) into a pharmaceutically acceptable salt, wherein R$^1$ and R$^2$ are as defined above. Preferably, X is Cl, Br, I, —O-mesylate or —O-tosylate.

Another preferred embodiment of the present invention relates to intermediate compounds of the processes as described above, particularly to the compound hydroxy-(4-hydroxy-benzo[b]thiophen-7-yl)acetate and the salts thereof with primary, secondary or tertiary amines. The compound hydroxy-(4-hydroxy-benzo[b]thiophen-7-yl)acetate and the salts thereof with tertiary amines are preferred, with the compounds hydroxy-(4-hydroxy-benzo[b]thiophen-7-yl)acetate and/or tributylammonium hydroxy-(4-hydroxy-benzo[b]thiophen-7-yl)acetate being particularly preferred.

A further preferred embodiment of the present invention relates to a process for the preparation of a compound of formula (IX)

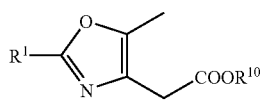
(IX)

comprising bromination of a compound of formula (X)

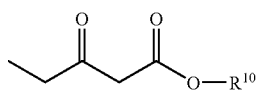
(X)

and subsequent condensation with an amide R$^1$C(O)NH$_2$ in the presence of an aliphatic alcohol, to obtain the compound of formula (IX), wherein R$^1$ is as defined above and R$^{10}$ is lower-alkyl. Preferably, R$^{10}$ is methyl or ethyl and the aliphatic alcohol is methanol or ethanol. Preferably, the aliphatic alcohol is a lower-alkyl-alcohol, in which the lower-alkyl group is preferably the same as in R$^{10}$. The compounds of formula (IX) are useful as an intermediate for the preparation of compounds of formula (VII).

The reaction of compounds of formula (II) with compounds of formula (III) as described above can be carried out according to methods known in the art, e.g. in a solvent such as mesitylene, toluene, DMF, THF, diethyl carbonate, propylene carbonate, N-methylpyrrolidone, tetramethylurea, α, α, α-trifluorotoluene, Dowtherm A, diphenylether, ethylene glycol diethylether, or ethylene glycol dimethylether, or in a mixture of such solvents. If the reaction is carried out in the presence of a base, Hünig base, triethylamine or tributylamine are suitable examples of such a base. The amount of base can conveniently be chosen in the range of 0.1 to 1.1, preferably 0.3 to 0.7 equivalents with reference to the educt.

The ratio of the compound of formula (II) to the compound of formula (III) can e.g. be 1/1.5. The reaction can be carried out as a batch or semibatch procedure or continuously in a tube reactor. A batch or semibatch procedure can conveniently be carried out at a reaction temperature between 100° C. and 280° C., preferably between 160° C. and 260° C. If the reaction is carried out continuously, a reaction temperature between 220° C. and 250° C. is convenient. In a continuous reaction, the flow rate is chosen so that 95% or more, preferably 99% or more, or even more preferably 99.5% or more of the educt are converted. Under the conditions and with the apparatus given in the examples, flow rates of 1 to 10 ml/min, preferably 4 to 5 ml/min can conveniently be chosen. Compounds of formula (III) are commercially available, known in the art, or can be prepared by methods known to the person skilled in the art.

The conversion of a compound of formula (I) into a pharmaceutically acceptable salt can be carried out by methods known in the art or in analogy to the examples described below.

The reaction of a compound of formula (V) with glyoxylic acid to yield a compound of formula (VI) as described above can e.g. be carried out as described in the examples. The reaction can be carried out in a solvent such as H$_2$O, DMSO, THF, toluene, or mixtures of such solvents, preferably in H₂O. The reaction can conveniently be carried out in the presence of a base such as e.g. NaOH, KOH, CsOH, Ca(OH)$_2$, tetrapropyl-NOH, trimethyl-benzyl-NOH, KO(tert.-butyl), DBU, tributylamine, preferably KOH. The base can e.g. be present in an amount of 1.75 to 2.4 equivalents, preferably 2.2 equivalents with reference to the compound of formula (V). The glyoxylic acid can be present in an amount of 0.75 to 1.4 equivalent, preferably about 1.2 equivalents with reference to the compound of formula (V) and can e.g. be provided as an aqueous solution of about 50% concentration. The reaction can e.g. be carried out at a temperature in the range of −10 to 25° C., preferably 0 to 5° C.

If desired, the compound of formula (VI) can be converted to a salt with a primary, secondary or tertiary amine, preferably a tertiary amine such as e.g. tributylamine, and isolated before subsequent reactions. The conditions for the formations of such salts are known in the art. The compound of formula (VI) or the above mentioned salt of a compound of formula (VI) can be converted to the compound of formula (IV) by oxidative decarboxylation. Such an oxidative decarboxylation can be carried out in a solvent such as e.g. H₂O and an optional co-solvent such as e.g. CH$_3$CN, DMF, ethanol, isopropanol, acetone or isopropylacetate, preferably isopropanol. The oxidative decarboxylation can be carried out with an oxidizing agent such as e.g. Fe$_2$(SO$_4$)$_3$, FeCl$_3$, Fe$_2$(SO$_4$)$_3$/H$_2$O$_2$ or CuCl$_2$, preferably Fe$_2$(SO$_4$)$_3$. An acid can be added to the reaction mixture, e.g. HCl or H$_2$SO$_4$, preferably H$_2$SO$_4$.

The reaction of a compound of formula (IV) with a compound of formula (VII) can be carried out by methods known to the person skilled in the art, e.g. in a solvent such as e.g. DMF or H₂O toluene, preferably in DMF. A base such as K$_2$CO$_3$, KO(tert.-butyl) or NaOH/tetrabutyl-NHSO$_4$, preferably K$_2$CO$_3$, can be present.

The reaction of a compound of formula (VIII) with thiazolidinedione can conveniently be carried out in an aromatic solvent such as e.g. toluene under reflux in the presence of an acid such as e.g. acetic acid, capronic acid or benzoic acid, preferably benzoic acid. A base such as e.g. piperidine, diisopropylamine, diethylamine, isobutylamine or di-n-butylamine, preferably piperidine, can furthermore be added to the reaction mixture.

The bromination of a compound of formula (X) can be carried out by a reaction with bromine, either without a solvent or in halogenated solvents such as dichloromethane, tetrachloromethane and benzotrifluoride, preferably in dichloromethane. The resulting bromide can be transformed in a subsequent condensation reaction with an amide R₁C(O)NH$_2$ in the presence of an aliphatic alcohol to yield a compound of formula (IX).

The following examples shall illustrate preferred embodiments of the present invention but are not intended to limit the scope of the invention. Starting materials are commercially available, known in the art, e.g. from EP1078923 or WO 01/79202, or can be prepared according to procedures well known to the person skilled in the art.

EXAMPLES

Example 1

Tributylammonium
Hydroxy-(4-hydroxy-benzo[b]thiophen-7-yl)-acetate

A 2 L reactor equipped with a mechanical stirrer, a thermometer, a dropping funnel, a sensor connected to a pH-meter and an argon inlet was charged under argon with 76.2 g (500 mmol) of 4-Hydroxybenzothiophene and 617.1 g (1100 mmol) of a 10% KOH aqueous solution. To the dark solution were added at 0-5° C. within 30 min ca. 85.91 g (580 mmol) of a 50% glyoxylic acid solution in water. If necessary, more glyoxylic acid is added such that the pH of the solution at the end of the addition was 11.5. After stirring for 3 h at 0-5° C., 200 ml of tert-butyl methyl ether were added to the reaction mixture followed by ca. 70 ml of 25% HCl solution in water such that the pH was ca. 7.0. The biphasic mixture was filtered through Speedex, then ca. 70 ml of 25% HCl solution in water were added to the aqueous phase such that the pH was ca. 2.0. After addition of 450 ml of tert-butyl methyl ether the organic phase was separated at room temperature and the aqueous phase washed with tert-butyl methyl ether. The combined organic phases were concentrated to a volume of ca. 300 ml and the residue was diluted with 50 ml of tert-butyl methyl ether and 100 ml of acetonitrile. To the resulting clear solution was added portionswise at 20-30° C. within 1 h a solution of 93.6 g (500 mmol) of tributylamine in 100 ml of tert-butyl methyl ether under seeding with crystals of the product. The resulting suspension was stirred over night at 20-30° C. and then filtered off. The filter cake was washed with 160 ml of tert-butyl methyl ether/acetonitrile 3:1 and the crystals dried over night at 60° C./10 mbar to afford 108.9 g (53.1%) of tributylammonium hydroxy-(4-hydroxy-benzo[b]thiophen-7-yl)-acetate as white crystals with a m.p. of ca. 200° C. (dec.).

Example 2

Synthesis of
4-hydroxy-benzo[b]thiophene-7-carboxaldehyde

A 750 ml, 4-necked glass flask equipped with a mechanical stirrer, a thermometer, a dropping funnel and an argon inlet was charged under argon with 41.0 g (100 mmol) of tributylammonium hydroxy-(4-hydroxy-benzo[b]thiophen-7-yl)-acetate, 60.5 g (115 mmol) of iron(III) sulfate and a mixture prepared from 60 ml of dry ethanol and 300 ml of 0.4 N sulfuric acid aqueous solution. Then stirring was started and the reaction mixture was heated to 55-60° C. for 5 h. After cooling to room temperature, 300 ml of isopropyl acetate and 100 ml of water were added under stirring, then the organic phase was separated and transferred into a 500 ml glass flask equipped with a pH meter. After addition of 150 ml of water (pH was 3.0), ca. 58 ml of a 2 N sodium hydroxide aqueous solution were added dropwise at 20° C. until a pH of 12-12.5 was reached. The organic phase was removed and to the aqueous phase were added at 10-15° C. dropwise ca. 54 ml of a 2 N aqueous solution of sulfuric acid until a pH of 4-4.5 was reached. The product precipitated during the addition. The suspension was stirred over night at room temperature, 1.2 h in an ice bath and then filtered. The filter cake was washed with water and dried at 60° C./15 mbar to afford 17.23 g (94%) of 4-hydroxy-benzo[b]thiophene-7-carboxaldehyde as white crystals with m.p. of 204° C.

Example 3

Synthesis of 4-[2-(5-methyl-2-phenyl-4-oxazolyl)
ethoxy]-benzo[b]thiophene-7-carboxaldehyde A 750 ml glass flask equipped with a thermometer, a stirrer and an argon inlet was charged under argon with 9.32 g (50 mmol) of 4-hydroxy-benzo[b]thiophene-7-carboxaldehyde, 7.60 g (55 mmol) of potassium carbonate and 135 ml of DMF. The resulting suspension was heated with stirring to 86° C., then a solution of 12.24 g (50 mmol) of 2-(5-methyl-2-phenyl)-4-oxazolyl)ethanol methanesulfonyl ester in 75 ml of DMF was added at this temperature within 60 min. The reaction mixture was stirred at the same temperature for 6 h, then 90 ml of toluene followed by 300 ml of water were added dropwise within 15 min, whereas the temperature was kept above 75° C. The aqueous phase was separated and extracted with 30 ml of warm toluene. The two toluene phases were combined, re-extracted with water, transferred into a 500 ml glass flask and finally treated with 180 ml of methanol. The resulting suspension was stirred over night at room temperature and 2 h at −13° C. Then the suspension was filtered, the filter cake was washed with toluene, cool methanol and finally dried at 60° C./10 mbar to afford 15.19 g (83%) of 4-[2-(5-methyl-2-phenyl-4-oxazolyl)ethoxy]-benzo[b]thiophene-7-carboxaldehyde as colorless crystals with a m.p. of 154° C.

Example 4

Synthesis of 4-[2-(5-methyl-2-phenyl-4-oxazolyl) ethoxy]-benzo[b]thiophene-7-carbaldehyde A 2 l, 4-necked glass reactor equipped with a mechanical stirrer, a thermometer, a cooler, a dropping funnel and an argon inlet was charged under argon in sequence with 103.2 g (250 mmol) of tributylammonium hydroxy-(4-hydroxy-benzo[b]thiophen-7-yl)-acetate, 151.3 g (287 mmol) of iron (III) sulfate, 150 ml of isopropanol, a mixture of 750 ml of water and 150 ml of 2 N sulfuric acid. The reaction mixture was heated under stirring to 63-65° C. for 2 h. After cooling to room temperature, 600 ml of isopropyl acetate were added and the mixture filtered. The filtrate was washed with 100 ml of water, then the organic phase was concentrated (ca. 470 ml were distilled off at 50° C./150-50 mbar). After addition of 625 ml of DMF, the rest of more volatile solvents are removed completely at 50° C./150-50 mbar. The water content at this point was less than 0.4%. This suspension containing the intermediate 4-hydroxy-benzo[b]thiophene-7-carboxaldehyde was transferred with aid of 660 ml of DMF in a 4 l reactor (equipped as the 2 l reactor above) which had been charged with 38.0 g of potassium carbonate. To the dark suspension was added within 60 min at 86-90° C. a solution of 70.4 g (250 mmol) of 2-(5-methyl-2-phenyl)-4-oxazolyl)ethanol methanesulfonyl ester in 275 ml of DMF. The reaction mixture was stirred at the same temperature for 6 h, then 450 ml of toluene followed by 950 ml of water were added, whereas the temperature was kept above 75° C. The aqueous phase was separated and extracted with 150 ml of warm toluene. The two toluene phases were combined, re-extracted with water and finally treated at a temperature between 65 and 40° C. with 900 ml of methanol. The resulting suspension was stirred for 1 h at 40° C., cooled to −15° C. and stirred for 3 h at −15° C. Finally the suspension was filtered, the filter cake was washed with 100 ml of a cold (−15° C.) toluene/methanol mixture and dried at 60° C./10 mbar to afford 76.8 g (84.5%) of 4-[2-(5-methyl-2-phenyl-4-oxazolyl)ethoxyl]-benzo[b]thiophene-7-carbaldehyde as colorless crystals with a m.p. of 154° C.

Example 5

Synthesis of 5-{[4-[2-(5-methyl-2-phenyl-4-oxazolyl)ethoxy]benzo[b]thien-7-yl]methylene}-2,4-thiazolidinedione A 4 l, 4-necked glass reactor equipped with a mechanical stirrer, a thermometer, a cooler, a dropping funnel, a water separator and an argon inlet was charged under argon in sequence with 115.0 g (300 mmol) of 4-[2-(5-Methyl-2-phenyl-oxazol-4-yl)-ethoxy]-benzo[b]thiophene-7-carbaldehyde, 44.4 g (375 mmol) of thiazolidinedione, 110.5 g (900 mmol) of benzoic acid and 2500 ml of toluene. After addition under stirring of 39.1 g (450 mmol) of piperidine, the suspension was stirred for 8 h at reflux whereas water was removed by collection in a separator. The suspension was cooled within 120 min under stirring to 0° C. and was stirred at this temperature over night. Finally the suspension was collected by filtration, the filter cake was washed with 500 ml of toluene and dried over night at 60° C./10 mbar, to afford 133.7 g (94.8%) of 5-[[4-[2-(5-methyl-2-phenyl-4-oxazolyl)ethoxy]benzo[b]thien-7-yl]methylene]-2,4-thiazolidinedione,as a yellow-orange crystalline material with a m.p. of 249° C.

Example 6

Synthesis of 5-{[4-[2-(5-methyl-2-phenyl-oxazol-4-yl)ethoxy]benzo[b]thiophen-7-yl]methyl}-2,4-thiazolidinedione A 2.5 l, 4-necked glass flask equipped with a mechanical stirrer, a thermometer, a cooler, a dropping funnel and an argon inlet was charged under argon in sequence with 118.2 g (250 mmol) of 5-[[4-[2-(5-methyl-2-phenyl-4-oxazolyl)ethoxy]benzo[b]thien-7-yl]methylene]-2,4-thiazolidinedione, 98.3 g (375 mmol) of 3,5-pyridinedicarboxylic acid, 1,4-dihydro-2,6-dimethyl-, diethyl ester, 563 ml of mesitylene and 17.4 ml (125 mmol) of triethylamine. The suspension was stirred at reflux (ca. 167° C.) for 6 h, then the resulting solution was cooled to 90° C. within 50 min, finally 1560 ml of ethanol were added within 10 min whereas the temperature dropped to 40° C. The suspension was cooled to 0° C. and stirred at this temperature for 5 h. Finally the precipitate was isolated by filtration, the filter cake was washed with 700 ml of ethanol and dried over night at 60° C./10 mbar, to afford 101.1 g (92.3%) of 5-{[4-[2-(5-methyl-2-phenyl-oxazol-4-yl)ethoxy]benzo[b]thiophen-7-yl]methyl}-2,4-thiazolidinedione as off-white crystalline material with a m.p. of 208° C.

Example 7

Synthesis of 5-{[4-[2-(5-methyl-2-phenyl-oxazol-4-yl)ethoxy]benzo[b]thiophen-7-yl]methyl}-2,4-thiazolidinedione A 1500 ml, 4-necked glass reactor with a mechanical stirrer, a thermometer, cooler and an argon inlet was charged under argon with 93.07 g (200 mmol) 5-[[4-[2-(5-methyl-2-phenyl-4-oxazolyl)ethoxy]benzo[b]thien-7-yl]methylene]-2,4-thiazolidinedione, and 125 ml of diphenylether.

A 1000 ml glass flask with double-walled jacket connected to a automatic heat regulator, with a mechanical stirrer, a thermometer, cooler, bottom discharge and argon inlet was charged under argon with 76.8 g (280 mmol) 3,5-pyridinedicarboxylic acid, 1,4-dihydro-2,6-dimethyl-, diethyl ester, and 200 ml diphenylether. From the bottom discharge a Teflon transfer line was installed to connect both glass vessels.

The content of the 1500 ml glass reactor was heated to 260° C. with a metal bath, while the content of the 1000 ml glass flask was heated to 145° C. The solution of 3,5-pyridinedicarboxylic acid, 1,4-dihydro-2,6-dimethyl-, diethyl ester was transferred within 1 to 2 minutes to the stirred solution of 5-[[4-[2-(5-methyl-2-phenyl-4-oxazolyl) ethoxy]-benzo[b]thien-7-yl]methylene]-2,4-thiazolidinedione. The temperature dropped to 220-230° C. and the mixture was heated again to 260° C. After 10 to 15 minutes 5-[[4-[2-(5-methyl-2-phenyl-4-oxazolyl)ethoxy]benzo[b]thien-7-yl]methylene]-2,4-thiazolidinedione was completely converted, and the metal bath removed. When the reaction mixture reached a temperature of 90° C., 650 ml of a mixture of n-heptane and ethanol (9:1) was added via a dropping funnel within 10 minutes. The mixture was seeded with 5-{[4-[2-(5-methyl-2-phenyl-oxazol-4-yl)ethoxy]benzo[b]thiophen-7-yl]methyl}-2,4-thiazolidinedione and crystallization started at 50° C. The suspension was cooled to 0° C. and stirred at that temperature for 5 h. The crystals were filtered off and washed with 4 portions of ethanol each 125 ml. The wet material was dried at 140° C., 10 mbar for 15 h, which afforded 89.1 g of white crystalline 5-{[4-[2-(5-methyl-2-phenyl-oxazol-4-yl)ethoxy]benzo[b]thiophen-7-yl]methyl}-2,4-thiazolidinedione with a purity of 96.5% according to HPLC analysis, corresponding to a corrected yield of 92.5%.

Example 8

Synthesis of 5-{[4-[2-(5-methyl-2-phenyl-oxazol-4-yl)ethoxy]benzo[b]thiophen-7-yl]methyl}-2,4-thiazolidinedione A 100 ml, 4-necked glass flask equipped with a mechanical stirrer, a thermometer, a cooler, a dropping funnel and an argon inlet was charged under argon in sequence with 9.20 g (19.6 mmol) of 5-[[4-[2-(5-methyl-2-phenyl-4-oxazolyl) ethoxy]benzo[b]thien-7-yl]methylene]-2,4-thiazolidinedione, 7.84 g (29.4 mmol) of 3,5-pyridinedicarboxylic acid, 1,4-dihydro-2,6-dimethyl-, diethyl ester and 43 ml of mesitylene. The suspension was stirred at reflux (ca. 167° C.) for 6 h, then the heating bath was removed. When the resulting suspension had a temperature of ca. 85° C. 125 ml of ethanol were added. After 2 h stirring at room temperature the precipitate was isolated by filtration, the filter cake was washed with 50 ml of ethanol and dried at 56° C./1 mbar for 2 h to afford 8.46 g (92%) of 5-{[4-[2-(5-methyl-2-phenyl-oxazol-4-yl)ethoxy]benzo[b]thiophen-7-yl]methyl}-2,4-thiazolidinedione as off-white crystalline material, which according to HPLC analysis had 99.3% purity.

Example 9

Synthesis of 5-{[4-[2-(5-methyl-2-phenyl-oxazol-4-yl)ethoxy]benzo[b]thiophen-7-yl]methyl}-2,4-thiazolidinedione A 35 ml stainless steel autoclave equipped with a magnetic stirring bar was charged under argon with 1.18 g (2.5 mmol) of 5-[[4-[2-(5-methyl-2-phenyl-4-oxazolyl)ethoxy]-benzo[b]thien-7-yl]methylene]-2,4-thiazolidinedione, 0.985 g (3.75 mmol) of 3,5-pyridinedicarboxylic acid, 1,4-dihydro-2,6-dimethyl-diethyl ester, 3.56 g of Dowtherm A and 0.18 ml (1.25 mmol) of triethylamine. The autoclave was closed and immersed into an oil bath at 230° C. The reaction was run with stirring (800 rpm) for 20 min, then the autoclave was cooled in water to room temperature, opened and a sample was taken from the clear, yellowish solution for HPLC analysis (conversion was 99.8%). The reaction mixture was transferred into a 50 ml round flask and the autoclave was rinsed with a total of 16 ml of ethanol. Immediately after the ethanol was added, crystals started to form. The yellowish suspension was stirred for 1 h at room temperature and in an ice bath (ca. 2° C.) for 4 h. The precipitate was filtered with suction, the filter cake was washed with a total of 7 ml of ethanol and dried (60° C., 25 mbar, 17 h) to afford 0.94 g (77.3%) of 5-{[4-[2-(5-methyl-2-phenyl-oxazol-4-yl)ethoxy]benzo[b]thiophen-7-yl]methyl}-2,4-thiazolidinedione as a yellowish solid, which according to quantitative HPLC analysis (column: XTerra TM RP18, 3.5 mm, Waters Art. 186000442, mob. phase pH 4.5 buffer/acetonitrile with gradient, flow 1 ml/min, UV detection, retention time of starting material 16.3 min, retention time of product 12.5 min) was 95.5% pure.

Example 10

Synthesis of 5-{[4-[2-(5-methyl-2-phenyl-oxazol-4-yl)ethoxy]benzo[b]thiophen-7-yl]methyl}-2,4-thiazolidinedione Apparatus sketch:

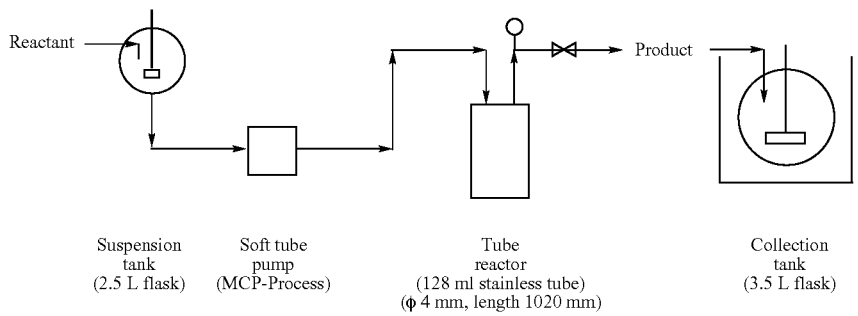

| Suspension tank (2.5 L flask) | Soft tube pump (MCP-Process) | Tube reactor (128 ml stainless tube) (φ 4 mm, length 1020 mm) | Collection tank (3.5 L flask) |

A 2.5 L 4-necked round-bottomed flask (suspension tank in the sketch) equipped with a mechanical stirrer was charged with 236.4 g of 5-[[4-[2-(5-methyl-2-phenyl-4-oxazolyl)ethoxy]benzo[b]thien-7-yl]methylene]-2,4-thiazolidinedione, (0.5 mol), 196.6 g of 3,5-pyridinedicarboxylic acid, 1,4-dihydro-2,6-dimethyl-diethyl ester (0.75 mol) and 750 g of Dowtherm A (20 w %, apparent density 1.132 g/ml). This mixture was stirred for ca. 2 h at room temperature until a homogeneous suspension was formed. The temperature of the tube reactor was set to 230° C. and was controlled automatically. When the temperature was reached, pumping of the reactant suspension was started at a flow rate of 4.8 ml/min. The effluent was collected with stirring in the collection tank which contained 2300 ml of ethanol. After 2 h, 661 g (i.e. 584 ml) of product solution had passed through the reactor, which corresponds to 132.2 g (0.28 mol) of 5-[[4-[2-(5-methyl-2-phenyl-4-oxazolyl)ethoxy]benzo[b]thien-7-yl]methylene]-2,4-thiazolidinedione. Crystallization of the product in the collection tank took place almost immediately after the addition of the effluent to the ethanol had started. Finally, the suspension was stirred for additional 14 h at room temperature and in an ice bath at ca. 2° C. for 4 h. The precipitate was filtered with suction, the filter cake was washed twice with a total of 1500 ml of cold (0° C.) ethanol and dried to constant weight (60° C., 25 mbar, 17 h) to afford 124.9 g (yield: 95.9%, 99.9% purity based on HPLC assay) of 5-{[4-[2-(5-methyl-2-phenyl-oxazol-4-yl)ethoxy]benzo[b]thiophen-7-yl]methyl}-2,4-thiazolidinedione as a yellowish solid.

Example 11

Synthesis of sodium 5-{[4-[2-(5-methyl-2-phenyl-oxazol-4-yl)ethoxy]benzo[b]thiophen-7-yl]methyl}2,4-thiazolidinedionate A 1000 ml round-bottomed glass flask was charged under argon with 46.62 g (100 mmol) of 5-{[4-[2-(5-methyl-2-phenyl-oxazol-4-yl)ethoxy]benzo[b]thiophen-7-yl]methyl}-2,4-thiazolidinedione and 600 ml of THF. The suspension was heated to 60° C. and filtered, the filter was washed with 50 ml of THF. To the clear solution were added under stirring 25.7 g (97 mmol) of a 15% sodium hydroxide aqueous solution. The turbid mixture was heated to reflux and a total of 1050 ml of THF was distilled off whereas additional 1050 ml of THF were added dropwise. The resulting suspension was cooled to 0° C. and stirred at this temperature for 2 h. Then the precipitate was filtered off, the filter cake was washed with 200 ml of THF and dried over night at 60° C./10 mbar, to afford 46.78 g (96.1%) of sodium 5-{[4-[2-(5-methyl-2-phenyl-oxazol-4-yl)ethoxy]benzo[b] 7-yl]methyl}2,4-thiazolidinedionate as white crystalline material with a m.p. of >250° C.

Example 12

Synthesis of 5-methyl-2-phenyl-oxazole-4-carboxylic acid ethyl ester

A 1 L double jacketed glass reactor equipped with a mechanical stirrer, a thermometer, a reflux condenser, a dropping funnel and an argon inlet was charged under argon with 84.4 g of 3-oxo-pentanoic acid methyl ester and 263 g of dichloromethane. The solution was cooled to 10° C. and a solution of 102.1 g bromine in 198 g of dichloromethane was added within 40 min. The dropping funnel was rinsed with 65 dichloromethane, then jacket temperature was set to 70° C. and solvent was completely distilled off. To the residue 120.0 g of benzamide, 564 g of toluene and 7.9 g of ethanol were added. The jacket temperature was set to 120° C. and 277 g of ethanol was dosed continuously to the reaction mixture within 12 h. Volatiles were distilled off during the reaction. After cooling to 90° C. 126 g of ethanol was added and the reaction mixture was stirred for 1 h. After distilling off the solvents the reaction mixture was cooled to 25° C. and 411 g of aqueous sodium carbonate and 521 g of tert-butylmethyl ether was added. The phases were separated and the organic layer was washed with 310 g of water. 106 g of toluene was added and tert-butylmethyl ether was distilled off. After cooling to 0° C. residual benzamide was crystallized and removed by filtration. The filter cake was washed with 75 g of toluene to afford a solution of 286.8 g (75% yield) 5-methyl-2-phenyl-oxazole-4-carboxylic acid ethyl ester in toluene.

The invention claimed is:

1. A process for the preparation of compounds of formula (I)

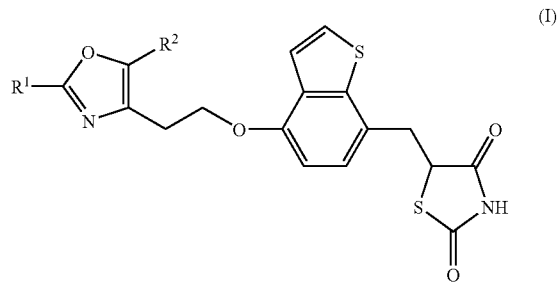

comprising reacting a compound of formula (II)

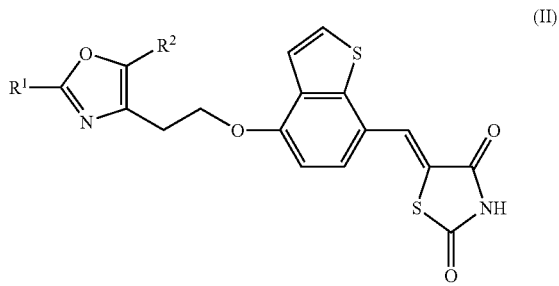

with a compound of formula (III)

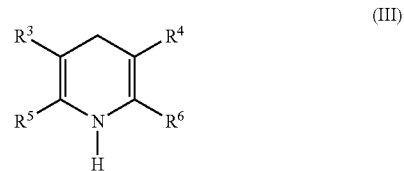

to yield the compound of formula (I),
wherein
  $R^1$ is aryl or heteroaryl,
  $R^2$ is lower-alkyl,
  $R^3$ is $COOR^7$,
  $R^4$ is $COOR^8$,
  $R^5$ and $R^6$ independently from each other are lower-alkyl, fluoro-lower-alkyl, aryl or —$CH_2$-aryl,
  $R^7$ and $R^8$ independently from each other are lower-alkyl, cycloalkyl, aryl or —$CH_2$-aryl, or $R^3$ and $R^5$ together are —CH=CH—CH=CH— to form a benzene ring together with the carbon atoms to which they are attached and $R^4$ and $R^6$ together are —CH=CH—CH=CH— to form a benzene ring together with the carbon atoms to which they are attached.

2. The process of claim 1, further comprising converting the compound of formula (I) into a pharmaceutically acceptable salt.

3. The process of claim 1, wherein $R^1$ is phenyl.

4. The process of claim 1, wherein $R^2$ is methyl.

5. The process of claim 1, wherein $R^1$ is phenyl and $R^2$ is methyl.

6. The process of claim 1, wherein $R^3$ is $COOR^7$, $R^4$ is $COOR^8$ and $R^7$ and $R^8$ independently from each other are lower-alkyl.

7. The process of claim 6, wherein $R^7$ and $R^8$ are methyl.

8. The process of claim 1, wherein $R^5$ and $R^6$ independently from each other are lower-alkyl.

9. The process of claim 8, wherein $R^5$ and $R^6$ are methyl.

10. The process of claim 1, which is carried out at a reaction temperature between 100° C. and 280° C.

11. The process of claim 10, which is carried out at a reaction temperature between 160° C. and 260° C.

12. The process of claim 11, which is carried out continuously at a reaction temperature between 220° C. and 250° C.

13. The process of claim 1, which is carried out in a solvent selected from the group consisting of 1,3,5-trimethylbenzene, diphenylether and Dowtherm A.

14. The process of claim 1, which is carried out in the presence of a base.

15. The process of claim 14, wherein the base is selected from the group consisting of Hünig base, triethylamine and tributylamine.

16. The process of claim 1, wherein the compound of formula (I) is converted into a sodium salt.

17. The process of claim 16, wherein the compound of formula (I) is converted into a sodium salt by reaction with sodium hydroxide in THF.

18. The process of claim 1 further comprising preparing the compound of formula (II) comprising reacting a compound of formula V

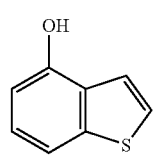

(V)

with glyoxylic acid to yield a compound of formula (VI)

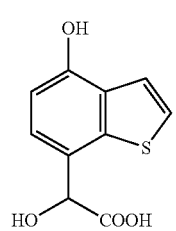

(VI)

and subsequent oxidative decarboxylation of the compound of formula (VI), to obtain the compound of formula (IV)

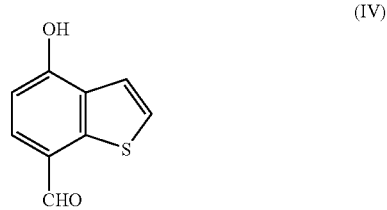

(IV)

and further reacting the compound of formula (IV) with a compound of formula (VII)

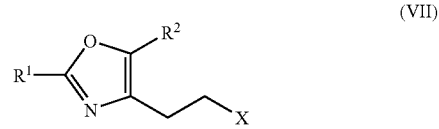

(VII)

wherein X is halogen or —O—$SO_2$—$R^9$, wherein $R^9$ is selected from the group consisting of lower alkyl, aryl and trifluoromethyl, to yield a compound of formula (VIII),

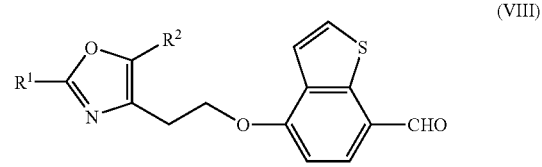

(VIII)

and further reacting the compound of formula (VIII) with thiazolidinedione to yield a compound of formula (II)

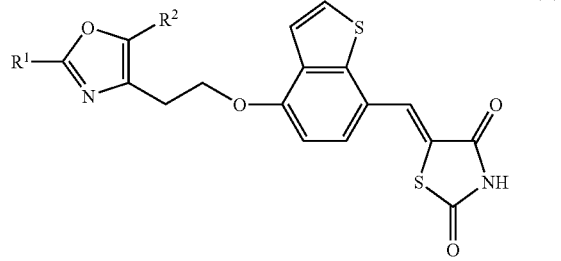

(II)

and converting the compound of formula (II) to the compound of formula (I) by a process according to claim 1, wherein $R^1$ and $R^2$ are as defined in claim 1.

19. The process of claim 18, further comprising converting the compound of formula (I) into a pharmaceutically acceptable salt.

* * * * *